US012297259B2

(12) United States Patent
Kumar et al.

(10) Patent No.: US 12,297,259 B2
(45) Date of Patent: May 13, 2025

(54) ASPERGILLUS ANTIGEN CHIMERIC RECEPTORS AND USE THEREOF

(71) Applicant: Board of Regents, The University of Texas System, Austin, TX (US)

(72) Inventors: Pappanaicken Kumar, Houston, TX (US); Thiago Aparecido Da Silva, Houston, TX (US); Paul J. Hauser, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 802 days.

(21) Appl. No.: 17/429,106

(22) PCT Filed: Feb. 7, 2020

(86) PCT No.: PCT/US2020/017181
§ 371 (c)(1),
(2) Date: Aug. 6, 2021

(87) PCT Pub. No.: WO2020/163695
PCT Pub. Date: Aug. 13, 2020

(65) Prior Publication Data
US 2022/0127340 A1    Apr. 28, 2022

Related U.S. Application Data

(60) Provisional application No. 62/802,540, filed on Feb. 7, 2019.

(51) Int. Cl.
| | | |
|---|---|---|
| *C07K 16/14* | (2006.01) |
| *A61K 39/00* | (2006.01) |
| *A61K 45/06* | (2006.01) |
| *C07K 14/705* | (2006.01) |
| *C07K 14/725* | (2006.01) |
| *G01N 33/569* | (2006.01) |

(52) U.S. Cl.
CPC ............ *C07K 16/14* (2013.01); *A61K 39/461* (2023.05); *A61K 39/4631* (2023.05); *A61K 39/4641* (2023.05); *A61K 45/06* (2013.01); *C07K 14/7051* (2013.01); *C07K 14/70521* (2013.01); *G01N 33/56961* (2013.01); *A61K 2239/13* (2023.05); *C07K 2317/622* (2013.01); *C07K 2319/02* (2013.01); *C07K 2319/03* (2013.01); *G01N 2333/38* (2013.01)

(58) Field of Classification Search
None
See application file for complete search history.

(56) References Cited

U.S. PATENT DOCUMENTS 5,807,559 A    9/1998 Jondal
2012/0263719 A1    10/2012 Mirelman et al.
2015/0018532 A1    1/2015 Thornton
2017/0224798 A1    8/2017 Cooper et al.
2018/0265595 A1    9/2018 Cooper et al.

OTHER PUBLICATIONS

Kumaresan et al. Methods of Controlling Invasive Fungal Infections Using CD8+ T Cells. Front. Immunol. 2017; 8:1939 1-14. (Year: 2017).*
Lopez-Medrano et al. Aspergillus fumigatus antigens. Microbiol 1995; 141:2699-2704. (Year: 1995).*
Casadevall, A. et al., "Characterization of a Murine Monoclonal Antibody to Crytococcus neoformans Polysaccharide that is a candidate for human therapeutic studies," Antimicrobial agents and chemotherapy, vol. 42, (6): 1437-1446, 1998.
Dos Santos, M. H. et al. "Titan Cells and Yeast Forms of Cryptococcus neoformans and Cryptococcus gattii Are Recognized by GXMR-CAR," *Microorganisms*, 9 (2021): 1-10.
Dos Santos, M. H. et al. "Modification of Hinge/Transmembrane and Signal Transduction Domains Improves the Expression and Signaling Threshold of GXMR-CAR Specific to *Cryptococcus* spp.," *Cells*, 11 (2022): 1-20.
Kumaresan et al., "Bioengineering T cells to target carbohydrate to treat opportunistic fungal infection," *Proc Natl Acad Sci U S A*, 111.29 (2014):10660-10665.
Kumaresan, P. R. et al., "Methods for Controlling Invasive Fungal Infections Using CD8+ T Cells," *Frontiers in Immunology*, 8 (2018): 1-14.
Liu, T. et al., "Glucuronoxylomannan promotes the generation of antigen-specific T regulatory cell that suppresses the antigen-specific Th2 response upon activation," *J. Cell. Mol. Med.*, 13.8B (2009): 1765-1774.
Lopez-Medrano et al., "Aspergillus fumigatus antigens," *Microbiology*, (1995): 2699-2704.
Mikulska, M. et al. "The use of mannan antigen and anti-mannan antibodies in the diagnosis of invasive candidiasis: recommendations from the Third European Conference on Infections in Leukemia," *Critical Care*, 14 (2010): 1-14.
PCT International Search Report and Written Opinion issued in International Application No. PCT/US2020/017181, dated May 13, 2020.
Saijo, S. et al., "Dectin-2 Recognition of α-Mannans and Induction of Th17 Cell Differentiation Is Essential for Host Defense against Candida albicans," *Immunity*, 32 (2010): 681-691.
Seif, M. et al., "CAR T cells targeting *Aspergillus fumigatus* are effective at treating invasive pulmonary aspergillosis in preclinical models," *Sci Transl Med.*, 14.664 (2022): 1-15.
Zhong, Z. et al., "Antifungal Activity of a Human Antiglucuronoxylomannan Antibody," *American Society for Microbiology*, 5.1 (1998): 58-64.

(Continued)

*Primary Examiner* — Daniel E Kolker
*Assistant Examiner* — Maureen Varina Driscoll
(74) *Attorney, Agent, or Firm* — Parker Highlander PLLC

(57) ABSTRACT

Provided herein is an antibody as well as chimeric antigen receptor (CAR) to the *Aspergillus* antigen p60-binding domain. Further provided herein are immune cells expressing the CARs as well as methods of their use in the treatment of fungal infections and cancer.

20 Claims, 5 Drawing Sheets
Specification includes a Sequence Listing.

(56) References Cited

OTHER PUBLICATIONS

Curran, K. J. et al., "Chimeric antigen receptors for T cell immunotherapy: current understanding and future directions," *The Journal of Gene Medicine*, 14 (2012): 405-415.
Janeway, C. A. et al., "Immunology: The Immune System in Health and Disease," 5$^{th}$ edition (2001): excerpt.
Rudikoff, S. et al., "Single amino acid substitution altering antigen-binding specificity," *Proc. Natl. Acad. Sci. USA*, 79 (1982): 1979-1983.
Sadelain, M. et al., "The basic principles of chimeric antigen receptor (CAR) design," *Cancer Discov.*, 3.4 (2013): 388-398.

* cited by examiner

SEQUENCE LISTING

<160> NUMBER OF SEQ ID NOS: 19

<210> SEQ ID NO 1
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 1

```
atggattttc aagtgcagat tttcagcttc ctgctaatca gtgcctcagt cataatatcc    60
agaggacaaa ttgttctcac ccagtctcca gcaatcatgt ctgcatttcc aggggagaag   120
gtcaccatga cctgtagtgt cagctcaagg gtaagataca tgcactggta ccagcagaag   180
tcaggcacct cccccaaaag atggatttat gacacatcca aactggcttc tggagtccct   240
gctcgcttca gtggcagtgg gtctgggacc tcttactctc tcacaatcag caacatggag   300
gctgaagatg ctgccactta ttactgccag cagtggagta gtcacccatt cacgttcggc   360
tcggggacaa agttggaaat aaaa                                           384
```

<210> SEQ ID NO 2
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 2

```
agtgtcagct caagggtaag atacatgcac                                      30
```

<210> SEQ ID NO 3
<211> LENGTH: 21
<212> TYPE: DNA
<213> ORGANISM: Artificial sequence
<220> FEATURE:

<223> OTHER INFORMATION: Synthetic oligonucleotide

<400> SEQUENCE: 3
gacacatcca aactggcttc t                                                21

<210> SEQ ID NO 4
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 4
cagcagtgga gtagtcaccc attcacg                                          27

<210> SEQ ID NO 5
<211> LENGTH: 128
<212> TYPE: PRT
<213> ORGANISM: Artificial sequence
<220> FEATURE:
<223> OTHER INFORMATION: Synthetic amino acid

<400> SEQUENCE: 5

Met Asp Phe Gln Val Gln Ile Phe Ser Phe Leu Leu Ile Ser Ala Ser
1               5                   10                  15

Val Ile Ile Ser Arg Gly Gln Ile Val Leu Thr Gln Ser Pro Ala Ile
            20                  25                  30

Met Ser Ala Phe Pro Gly Glu Lys Val Thr Met Thr Cys Ser Val Ser
        35                  40                  45

Ser Arg Val Arg Tyr Met His Trp Tyr Gln Gln Lys Ser Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Asn Met Glu Ala Glu Asp Ala Ala Thr Tyr Tyr Cys Gln Gln Trp
            100                 105                 110

Ser Ser His Pro Phe Thr Phe Gly Ser Gly Thr Lys Leu Glu Ile Lys
        115                 120                 125

<210> SEQ ID NO 6
<211> LENGTH: 411
<212> TYPE: DNA
<213> ORGANISM: Artificial sequence
<220> FEATURE:
<223> OTHER INFORMATION: Synthetic oligonucleotide

<400> SEQUENCE: 6
atggattttg ggctgatttt ttttattgtt gctcttttaa aaggggtcca gtgtgaaata      60
aaacttctcg agtctggagg tggcctggtg cagcctggag gatccctgaa actctcctgt    120
gcagcctcag gattcgattt tagtagatat tggatggctt gggtccggca ggctccaggg    180
aaagggctag aatggattgg agaaattaat ccagctagca gtacgataaa ctatacgcca    240
tctctaaagg atcacttcat catctccaga gacaacgcca aaatacgct gtatctgcaa     300 atgagcaaaa tgagatctga ggacacagcc ctttattact gtgcaagacc ggacggtaac    360
ccctatgcta tggattattg gggtcaaggc acctcagtca ccgtctcctc a              411

<210> SEQ ID NO 7
<211> LENGTH: 15

```
<212> TYPE: DNA
<213> ORGANISM: Artificial sequence
<220> FEATURE:
<223> OTHER INFORMATION: Synthetic oligonucleotide

<400> SEQUENCE: 7
agatattgga tggct                                                    15

<210> SEQ ID NO 8
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 8
gaaattaatc cagctagcag tacgataaac tatacgccat ctctaaagga t            51

<210> SEQ ID NO 9
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 9
ccggacggta acccctatgc tatggattat                                    30

<210> SEQ ID NO 10
<211> LENGTH: 137
<212> TYPE: PRT
<213> ORGANISM: Artificial sequence
<220> FEATURE:
<223> OTHER INFORMATION: Synthetic amino acid

<400> SEQUENCE: 10

Met Asp Phe Gly Leu Ile Phe Phe Ile Val Ala Leu Leu Lys Gly Val
1               5                   10                  15

Gln Cys Glu Ile Lys Leu Leu Glu Ser Gly Gly Gly Leu Val Gln Pro
            20                  25                  30

Gly Gly Ser Leu Lys Leu Ser Cys Ala Ala Ser Gly Phe Asp Phe Ser
        35                  40                  45

Arg Tyr Trp Met Ala Trp Val Arg Gln Ala Pro Gly Lys Gly Leu Glu
    50                  55                  60

Trp Ile Gly Glu Ile Asn Pro Ala Ser Ser Thr Ile Asn Tyr Thr Pro
65                  70                  75                  80

Ser Leu Lys Asp His Phe Ile Ile Ser Arg Asp Asn Ala Lys Asn Thr
                85                  90                  95

Leu Tyr Leu Gln Met Ser Lys Met Arg Ser Glu Asp Thr Ala Leu Tyr
            100                 105                 110

Tyr Cys Ala Arg Pro Asp Gly Asn Pro Tyr Ala Met Asp Tyr Trp Gly
        115                 120                 125

Gln Gly Thr Ser Val Thr Val Ser Ser
    130                 135

<210> SEQ ID NO 11
<211> LENGTH: 730
<212> TYPE: DNA
<213> ORGANISM: Artificial sequence
<220> FEATURE:
<223> OTHER INFORMATION: Synthetic oligonucleotide

<400> SEQUENCE: 11
```

```
caaattgttc tcacccagtc tccagcaatc atgtctgcat ttccagggga gaaggtcacc    60
atgacctgta gtgtcagctc aagggtaaga tacatgcact ggtaccagca gaagtcaggc   120
acctccccca aaagatggat ttatgacaca tccaaactgg cttctggagt ccctgctcgc   180
ttcagtggca gtgggtctgg gacctcttac tctctcacaa tcagcaacat ggaggctgaa   240
gatgctgcca cttattactg ccagcagtgg agtagtcacc cattcacgtt cggctcgggg   300
acaaagttgg aaataaaagg cagcacctcc ggcagcggca agcctggcag cggcgagggc   360
agcaccaagg gcgaaataaa acttctcgag tctggaggtg gcctggtgca gcctggagga   420
tccctgaaac tctcctgtgc agcctcagga ttcgatttta gtagatattg gatggcttgg   480
gtccggcagg ctccagggaa agggctagaa tggattggag aaattaatcc agctagcagt   540
acgataaact atacgccatc tctaaaggat cacttcatca tctccagaga caacgccaaa   600
aatacgctgt atctgcaaat gagcaaaatg agatctgagg acacagccct ttattactgt   660
gcaagaccgg acggtaaccc ctatgctatg gattattggg gtcaaggcac ctcagtcacc   720
gtctcctcaa                                                         730

<210> SEQ ID NO 12
<211> LENGTH: 243
<212> TYPE: PRT
<213> ORGANISM: Artificial sequence
<220> FEATURE:
<223> OTHER INFORMATION: Synthetic amino acid

<400> SEQUENCE: 12

Gln Ile Val Leu Thr Gln Ser Pro Ala Ile Met Ser Ala Phe Pro Gly
1               5                   10                  15

Glu Lys Val Thr Met Thr Cys Ser Val Ser Ser Arg Val Arg Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Trp Ser Ser His Pro Phe Thr
                85                  90                  95

Phe Gly Ser Gly Thr Lys Leu Glu Ile Lys Gly Ser Thr Ser Gly Ser
            100                 105                 110

Gly Lys Pro Gly Ser Gly Glu Gly Ser Thr Lys Gly Glu Ile Lys Leu
        115                 120                 125

Leu Glu Ser Gly Gly Gly Leu Val Gln Pro Gly Gly Ser Leu Lys Leu
    130                 135                 140

Ser Cys Ala Ala Ser Gly Phe Asp Phe Ser Arg Tyr Trp Met Ala Trp
145                 150                 155                 160

Val Arg Gln Ala Pro Gly Lys Gly Leu Glu Trp Ile Gly Glu Ile Asn
                165                 170                 175

Pro Ala Ser Ser Thr Ile Asn Tyr Thr Pro Ser Leu Lys Asp His Phe
            180                 185                 190

Ile Ile Ser Arg Asp Asn Ala Lys Asn Thr Leu Tyr Leu Gln Met Ser
        195                 200                 205

Lys Met Arg Ser Glu Asp Thr Ala Leu Tyr Tyr Cys Ala Arg Pro Asp
    210                 215                 220
```

Gly Asn Pro Tyr Ala Met Asp Tyr Trp Gly Gln Gly Thr Ser Val Thr
225                 230                 235                 240

Val Ser Ser

<210> SEQ ID NO 13
<211> LENGTH: 56
<212> TYPE: DNA
<213> ORGANISM: Artificial sequence
<220> FEATURE:
<223> OTHER INFORMATION: Synthetic oligonucleotide

<400> SEQUENCE: 13
caccggcgaa ggaggcctat catgaagatc tatcgattgt acagctagcc gccacc        56

<210> SEQ ID NO 14
<211> LENGTH: 56
<212> TYPE: DNA
<213> ORGANISM: Artificial sequence
<220> FEATURE:
<223> OTHER INFORMATION: Synthetic oligonucleotide

<400> SEQUENCE: 14
caccggcgaa ggaggcctat catgaagatc tatcgattgt acagctagcc gccacc        56

<210> SEQ ID NO 15
<211> LENGTH: 690
<212> TYPE: DNA
<213> ORGANISM: Artificial sequence
<220> FEATURE:
<223> OTHER INFORMATION: Synthetic oligonucleotide

<400> SEQUENCE: 15
gagagcaagt acggccctcc ctgcccccct tgccctgccc ccgagttcga gggcggaccc        60
agcgtgttcc tgttcccccc caagcccaag gacaccctga tgatcagccg gaccccggag       120
gtgacctgtg tggtggtgga cgtgtcccag gaggaccccg aggtccagtt caactggtac       180
gtggacggcg tggaggtgca acgccaag accaagcccc gggaggagca gttccagagc         240
acctaccggg tggtgtccgt gctgaccgtg ctgcaccagg actggctgaa cggcaaggaa       300
tacaagtgta aggtgtccaa caagggcctg cccagcagca tcgagaaaac catcagcaag       360
gccaagggcc agcctcggga gccccaggtg tacaccctgc ccctagcca agaggagatg        420 accaagaatc aggtgtccct gacctgcctg gtgaagggct tctacccag cgacatcgcc       480 gtggagtggg agagcaacgg ccagcccgag aacaactaca agaccacccc ccctgtgctg      540
gacagcgacg gcagcttctt cctgtacagc aggctgaccg tggacaagag ccggtggcag      600
gagggcaacg tctttagctg ctccgtgatg cacgaggccc tgcacaacca ctacacccag      660
aagagcctgt ccctgagcct gggcaagatg                                      690

<210> SEQ ID NO 16
<211> LENGTH: 81
<212> TYPE: DNA
<213> ORGANISM: Artificial sequence
<220> FEATURE:
<223> OTHER INFORMATION: Synthetic oligonucleotide

<400> SEQUENCE: 16
ttctgggtgc tggtcgtggt gggtggcgtg ctggcctgct acagcctgct ggtgacagtg        60
gccttcatca tcttttgggt g                                                  81

<210> SEQ ID NO 17

```
<211> LENGTH: 123
<212> TYPE: DNA
<213> ORGANISM: Artificial sequence
<220> FEATURE:
<223> OTHER INFORMATION: Synthetic oligonucleotide

<400> SEQUENCE: 17
aggagcaagc ggagcagagg cggccacagc gactacatga acatgacccc ccggaggcct    60
ggccccaccc ggaagcacta ccagccctac gcccctccca gggacttcgc cgcctaccgg   120
agc                                                                 123

<210> SEQ ID NO 18
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 18
cgggtgaagt tcagccggag cgccgacgcc cctgcctacc agcagggcca gaaccagctg    60
tacaacgagc tgaacctggg ccggagggag gagtacgacg tgctggacaa gcggagaggc   120
cgggaccctg agatgggcgg caagcccagg agaaagaacc ctcaggaggg cctgtataac   180
gaactgcaga agacaagat ggccgaggcc tacagcgaga tcggcatgaa gggcgagcgg   240
cggaggggca agggccacga cggcctgtac cagggcctga gcaccgccac caaggatacc   300
tacgacgccc tgcacatgca ggccctgccc cccagatga                          339

<210> SEQ ID NO 19
<211> LENGTH: 2069
<212> TYPE: DNA
<213> ORGANISM: Artificial sequence
<220> FEATURE:
<223> OTHER INFORMATION: Synthetic oligonucleotide

<400> SEQUENCE: 19
gtacagcttc gaatagccgc caccatgctg ctgctggtga ccagcctgct gctgtgtgag    60
ctgccccacc ccgcctttct gctgatcccc caaattgttc tcacccagtc tccagcaatc   120
atgtctgcat ttccagggga aaggtcacc atgacctgta gtgtcagctc aagggtaaga   180
tacatgcact ggtaccagca gaagtcaggc acctccccca aaagatggat ttatgacaca   240
tccaaactgg cttctggagt ccctgctcgc ttcagtggca gtgggtctgg gacctcttac   300
tctctcacaa tcagcaacat ggaggctgaa gatgctgcca ttattactg ccagcagtgg   360 agtagtcacc cattcacgtt cggctcgggg acaaagttgg aaataaaagg cagcacctcc   420
ggcagcggca agcctggcag cggcgagggc agcaccaagg gcgaaataaa acttctcgag   480
tctggaggtg gcctggtgca gcctggagga tccctgaaac tctcctgtgc agcctcagga   540
ttcgatttta gtagatattg gatggcttgg gtccggcagg ctccagggaa agggctagaa   600
tggattggag aaattaatcc agctagcagt acgataaact atgccatc tctaaaggat   660 cacttcatca tctccagaga caacgccaaa aatacgctgt atctgcaaat gagcaaaatg   720
agatctgagg acacagccct ttattactgt gcaagaccgg acgtaaccc ctatgctatg   780 gattattggg gtcaaggcac ctcagtcacc gtctcctcaa gcgagagcaa gtacggccct   840
ccctgccccc cttgccctgc ccccgagttc gagggcggac ccagcgtgtt cctgttcccc   900
cccaagccca aggacaccct gatgatcagc cggacccccg aggtgacctg tgtggtggtg   960
gacgtgtccc aggaggaccc cgaggtccag ttcaactggt acgtggacgg cgtggaggtg  1020
```

```
cacaacgcca agaccaagcc ccgggaggag cagttccaga gcacctaccg ggtggtgtcc    1080
gtgctgaccg tgctgcacca ggactggctg aacggcaagg aatacaagtg taaggtgtcc    1140
aacaagggcc tgcccagcag catcgagaaa accatcagca aggccaaggg ccagcctcgg    1200 gagcccagg tgtacaccct gcccctagc caagaggaga tgaccaagaa tcaggtgtcc      1260
ctgacctgcc tggtgaaggg cttctacccc agcgacatcg ccgtggagtg ggagagcaac    1320
ggccagcccg agaacaacta caagaccacc cccctgtgc tggacagcga cggcagcttc    1380
ttcctgtaca gcaggctgac cgtggacaag agccggtggc aggagggcaa cgtctttagc    1440
tgctccgtga tgcacgaggc cctgcacaac cactacaccc agaagagcct gtccctgagc    1500
ctgggcaaga tgttctgggt gctggtcgtg gtgggtggcg tgctggcctg ctacagcctg    1560
ctggtgacag tggccttcat catcttttgg gtgaggagca agcggagcag aggcggccac    1620
agcgactaca tgaacatgac cccccggagg cctggcccca cccggaagca ctaccagccc    1680
tacgcccctc ccagggactt cgccgcctac cggagccggg tgaagttcag ccggagcgcc    1740
gacgcccctg cctaccagca gggccagaac cagctgtaca acgagctgaa cctgggccgg    1800
agggaggagt acgacgtgct ggacaagcgg agaggccggg accctgagat gggcggcaag    1860
ccccggagaa agaaccctca ggagggcctg tataacgaac tgcagaaaga caagatggcc    1920
gaggcctaca gcgagatcgg catgaagggc gagcggcgga ggggcaaggg ccacgacggc    1980
ctgtaccagg gcctgagcac cgccaccaag gatacctacg acgccctgca catgcaggcc    2040 ctgccccca gatgatttaa ataactagt                                       2069
```

ASPERGILLUS ANTIGEN CHIMERIC RECEPTORS AND USE THEREOF

This application is a national phase application under 35 U.S.C. § 371 of International Application No. PCT/US2020/017181, filed Feb. 7, 2020, which claims the benefit of U.S. Provisional Patent Application No. 62/802,540, filed Feb. 7, 2019, each of which is incorporated herein by reference in its entirety.

The sequence listing that is contained in the file named "UTFCP1389WO_ST25.txt", which is 14 KB (as measured in Microsoft Windows®) and was created on Feb. 5, 2020, is filed herewith by electronic submission and is incorporated by reference herein.

BACKGROUND

1. Field

The present invention relates generally to the fields of immunology and molecular biology. More particularly, it concerns anti-fingal chimeric antigen receptors (CARs).

2. Description of Related Art

Fungal infections pose a significant threat to human population and affecting over a billion people worldwide. Despite available anti-fungal drugs, invasive fungal infections are associated with high mortality rates worldwide, causing an estimated 1.5 million deaths each year, a number comparable to tuberculosis. The most affected groups are immunocompromised patients such as those living with HIV/AIDs, cancer patients who are receiving chemotherapy, and solid organ transplant patients who are taking immunosuppressive drugs. *Candida, Aspergillus, Cryptococcus* sp. and pneumocystis account for 90% of the deaths caused by invasive fungal infections (IFI). Many currently available drugs face limitations, such as drug resistance, harmful side effects, and negative interactions with other drugs. Thus, there is no curative therapy to treat drug resistant IFI.

SUMMARY

In certain embodiments, the present disclosure provides an isolated monoclonal antibody, wherein the antibody specifically binds to *Aspergillus* antigen p60 and comprises (a) a first $V_H$ CDR is identical to SEQ ID NO: 7; (b) a second $V_H$ CDR is identical to SEQ ID NO: 8; (c) a third $V_H$ CDR is identical to SEQ ID NO: 9; (d) a first $V_L$, CDR is identical to SEQ ID NO: 2; (e) a second $V_L$, CDR is identical to SEQ ID NO: 3; and (f) a third $V_L$, CDR is identical to SEQ ID NO: 4;

In some aspects, the nucleotide sequences of the antibody comprise a $V_H$ domain at least about 80% (e.g., at least about 81%, 82%, 83%, 84%, 85%, 86%, 87%, 88%, 89%, 90%, 91%, 92%, 93%, 94%, 95%, 96%, 97%, 98%, or 99%) identical to the $V_H$ domain of AF269-5 (SEQ ID NO: 6) and a $V_L$, domain at least about 80% (e.g., at least about 81%, 82%, 83%, 84%, 85%, 86%, 87%, 88%, 89%, 90%, 91%, 92%, 93%, 94%, 95%, 96%, 97%, 98%, or 99%) identical to the $V_L$ domain of AF269-5 (SEQ ID NO: 1). In certain aspects, the nucleotide sequences of the antibody comprise a $V_H$ domain identical to the $V_H$ domain of AF269-5 (SEQ ID NO: 6) and a $V_L$ domain identical to the $V_L$ domain of AF269-5 (SEQ ID NO: 1). In certain aspects, the amino acid sequences of the antibody comprise a $V_H$ domain at least about 80% (e.g., at least about 81%, 82%, 83%, 84%, 85%, 86%, 87%, 88%, 89%, 90%, 91%, 92%, 93%, 94%, 95%, 96%, 97%, 98%, or 99%) identical to the $V_H$ domain of AF269-5 (SEQ ID NO: 10) and a $V_L$ domain at least about 80% (e.g., at least about 81%, 82%, 83%, 84%, 85%, 86%, 87%, 88%, 89%, 90%, 91%, 92%, 93%, 94%, 95%, 96%, 97%, 98%, or 99%) identical to the $V_L$ domain of AF269-5 (SEQ ID NO: 5). In particular aspects, the amino acid sequences of the antibody comprise a $V_H$ domain identical to the $V_H$ domain of AF269-5 (SEQ ID NO: 10) and a $V_L$ domain identical to the $V_L$ domain of AF269-5 (SEQ ID NO: 5).

In certain aspects, the antibody is recombinant. In some aspects, the antibody is an IgG, IgM, IgA or an antigen binding fragment thereof. In specific aspects, the antibody is a Fab', a F(ab')2, a F(ab')3, a monovalent scFv, a bivalent scFv, or a single domain antibody. In particular aspects, the antibody is a human, humanized antibody or de-immunized antibody. In some aspects, the antibody is conjugated to an imaging agent, a chemotherapeutic agent, a toxin or a radionuclide.

In another embodiment, there is provided a composition comprising an antibody of the embodiments (e.g., and antibody specifically binds to *Aspergillus* antigen p60) in a pharmaceutically acceptable carrier. A further embodiment provides a recombinant polypeptide comprising an antibody $V_H$ domain comprising CDRs 1-3 of the $V_H$ domain of AF269-5 (SEQ ID NOs: 7, 8, and 9) and an antibody $V_L$ domain comprising CDRs 1-3 of the $V_L$ domain of AF269-5 (SEQ ID NOs: 2, 3, and 4). Another embodiment provides a recombinant polypeptide comprising an antibody $V_H$ domain of AF269-5 (SEQ ID NO: 6) and an antibody $V_L$ domain of AF269-5 (SEQ ID NO:1).

A further embodiment provides a method for detecting *Aspergillus* Sp. Comprising (a) obtaining a sample from a subject; (b) contacting the sample with the antibody of the embodiments (e.g., and antibody specifically binds to *Aspergillus* antigen p60); and (c) detecting binding between the antibody and *Aspergillus* Sp. In particular aspects, the *Aspergillus* sp. is *A. fumigatus* or *A. avis*.

In yet another embodiment there is provided a chimeric antigen receptor (CAR) comprising an *Aspergillus* antigen p60-binding domain. In some aspects, the *Aspergillus* antigen p60-binding domain is selected from the group consisting of F(ab')2, Fab', Fab, Fv, and scFv. In certain aspects, the *Aspergillus* antigen p60-binding domain is an scFv. In some aspects, the scFv comprises an amino acid sequence with at least 80% (e.g., at least about 81%, 82%, 83%, 84%, 85%, 86%, 87%, 88%, 89%, 90%, 91%, 92%, 93%, 94%, 95%, 96%, 97%, 98%, or 99%) sequence identity to SEQ ID NO:12. In particular aspects, the scFv comprises an amino acid sequence of SEQ ID NO:12. In some aspects, the scFv is encoded by a nucleotide sequence with at least 80% (e.g., at least about 81%, 82%, 83%, 84%, 85%, 86%, 87%, 88%, 89%, 90%, 91%, 92%, 93%, 94%, 95%, 96%, 97%, 98%, or 99%) sequence identity to SEQ ID NO:11. In specific aspects, the scFv is encoded by a nucleotide sequence of SEQ ID NO:11.

In some aspects, the CAR comprises signaling domains CD3ζ, CD28, OX40/CD134, 4-1BB/CD137, TRAM, MyD88, TRAF 6, or a combination thereof. In some aspects, the CAR comprises signaling domains CD28 and CD3ζ. In particular aspects, the CAR comprises a CD28, CD8a, CD134, CD137, or TLR transmembrane domain. In some aspects, the CAR comprises a co-stimulatory domain selected from the group consisting of CD3ζ, FcR, CD27, CD28, CD30, CARD-9, CARD-10, CD137, DAP10, Toll-like receptor (TLR), OX40, NKp30, NKp46, NKp44, DAP12, NKG2D, CD160, KIR2DS1, CD16, CD226, NKp80, CS1 (CD319), and 2B4 (CD244). In particular aspects, the CAR comprises a CD28 transmembrane domain. In some aspects, the CAR comprises an IgG4-M spacer. In particular aspects, the CAR comprises the AF269-5 scFv, IgG4-M spacer, CD28 transmembrane domain, CD28 signaling domain, and CD3ζ signaling domain.

In some aspects, the CAR comprises a nucleotide sequence with at least 80% (e.g., at least about 81%, 82%, 83%, 84%, 85%, 86%, 87%, 88%, 89%, 90%, 91%, 92%, 93%, 94%, 95%, 96%, 97%, 98%, or 99%) sequence identity to SEQ ID NO:11. In specific aspects, the CAR comprises a nucleotide sequence of SEQ ID NO:11.

Further provided herein is an isolated polynucleotide encoding a CAR of the embodiments. In some aspects, the polynucleotide comprises SEQ ID NO:3. Also provided herein is an expression vector encoding a CAR of the embodiments. In some aspects, the vector is further defined as a viral vector. For example, the viral vector is a lentiviral vector.

Another embodiment provides a host cell engineered to express a CAR comprising a AF269-5 antigen-binding domain according to the embodiments. In some aspects, the host cell is further defined as an immune cell. In certain aspects, the immune cell is a T cell, lymphocyte, myelocyte, NK cell, macrophage, or dendritic cell. In some aspects, the T cell is a αβ T cell. In other aspects, the T cell is a γδ T cell. In some aspects, the T cell is a CD4, CD8, regulatory, T17, follicular helper (Tfh), Th1, or Th2 T cell. In certain aspects, the immune cell is derived from peripheral blood monocytes (PBMCs) or tumor microenvironment. In some aspects, the immune cell is a Jurkat cell, NK-92 cell, KHYG-1 cell, or U937 cell. The immune cell may be allogeneic or autologous. In some aspects, the immune cell is isolated from peripheral blood, cord blood, or bone marrow.

Further provided herein is a pharmaceutical composition comprising a population of cells of the embodiments.

Also provided herein is a composition comprising a population of cells of the embodiments for use in the treatment of a fungal infection.

Another embodiment provides a method of treating a fungal infection in a subject comprising administering an effective amount of cells of the embodiments to the subject. In some aspects, the fungal infection is an invasive fungal infection. In particular aspects, the invasive fungal infection is drug resistant. In specific aspects, the fungal infection is caused by *Aspergillus* sp. The cells may be autologous or allogeneic.

In some aspects, the subject is immunocompromised or immunocompetent. In particular aspects, the immunocompromised subject has been diagnosed with HIV/AIDS or cancer. In some aspects, the immunocompromised subject is undergoing chemotherapy or immunosuppressive therapy. In certain aspects, the immunocompromised subject is a transplant recipient. In some aspects, the subject is healthy and was injured in an accident or in a war field.

In additional aspects, the method further comprises administering at least a second anti-fungal agent. In some aspects, the at least a second anti-fungal agent is amphotericin B, caspofungin, isavuconazole, or posaconazole. In certain aspects, the cells and/or the at least a second anti-fungal agent are administered intravenously, intraperitoneally, intratracheally, intratumorally, intramuscularly, endoscopically, intralesionally, percutaneously, subcutaneously, regionally, or by direct injection or perfusion. In some aspects, the method further comprises administering an anti-viral agent.

Further provided herein are use of the AF269-5 CAR T cells to deliver biomolecules and/or synthetic pharmaceutical agents, such as anti-microbial peptides, growth factors, and/or cytokines such as IL-15, IL-12, IL-4, IL-10, IL-17A, or IFNγ, such as to boost the innate immune system at the infection site, to deliver synthetic anti-microbial, viral and/ or fungal agents.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 4A) Screening hybridoma clones by ELISA using anti-IgM specific antibodies. Serial dilutions are shown in X-axis and optical absorbance as optical density are shown in Y axis. Various anti-fungal hybridoma clones are shown on the right side. AF269-5 clone showed positivity at 1:3375 dilution factor compared to control clone 269-7. (FIG. 4B) Screening hybridoma clones by ELISA using anti-IgG specific antibodies. Serial dilutions are shown in X-axis and optical absorbance as optical density are shown in Y axis. Various anti-fungal hybridoma clones are shown on the right side. No clones show positivity at higher dilutions.

DESCRIPTION OF ILLUSTRATIVE EMBODIMENTS

Figure 1:
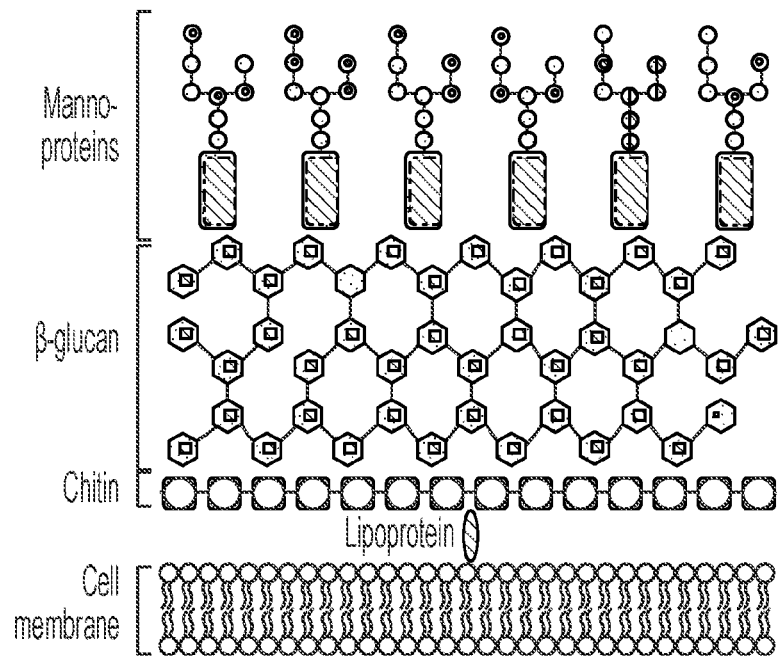
FIG. 1: A schematic diagram depicts general fungal cell wall structure. A single plasma membrane is also present in fungi, surrounded by a cell wall consisting of various layers of the polysaccharides chitin, β-glucan and AF269-5 (in the form of mannoproteins).
Figure 2:
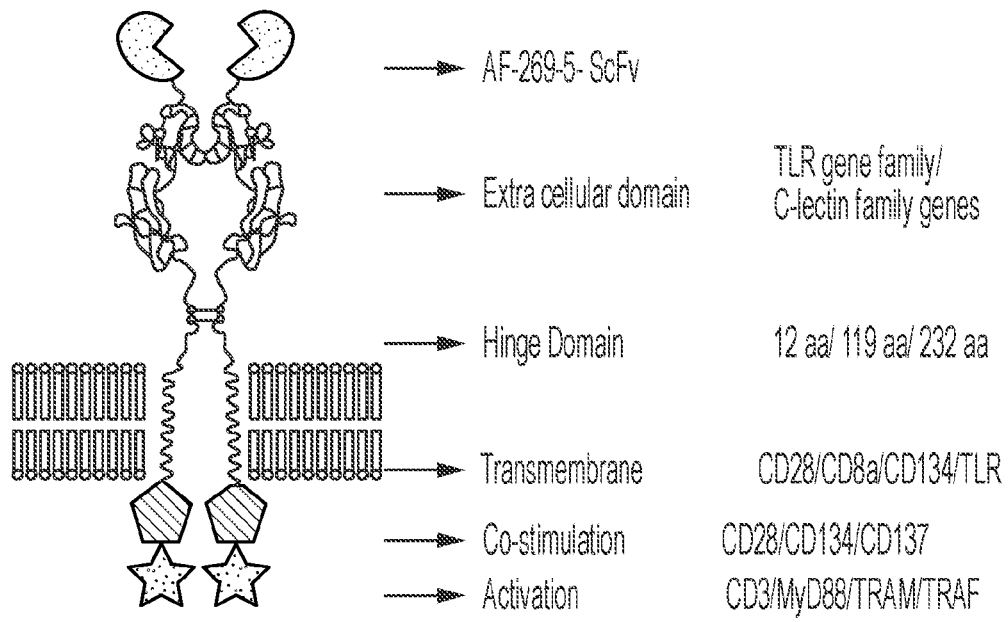
FIG. 2: A schematic representation of AF-269-5 CAR for anti-fungal therapy and the different permutations of genes used for the development of CARs.
Figure 3:
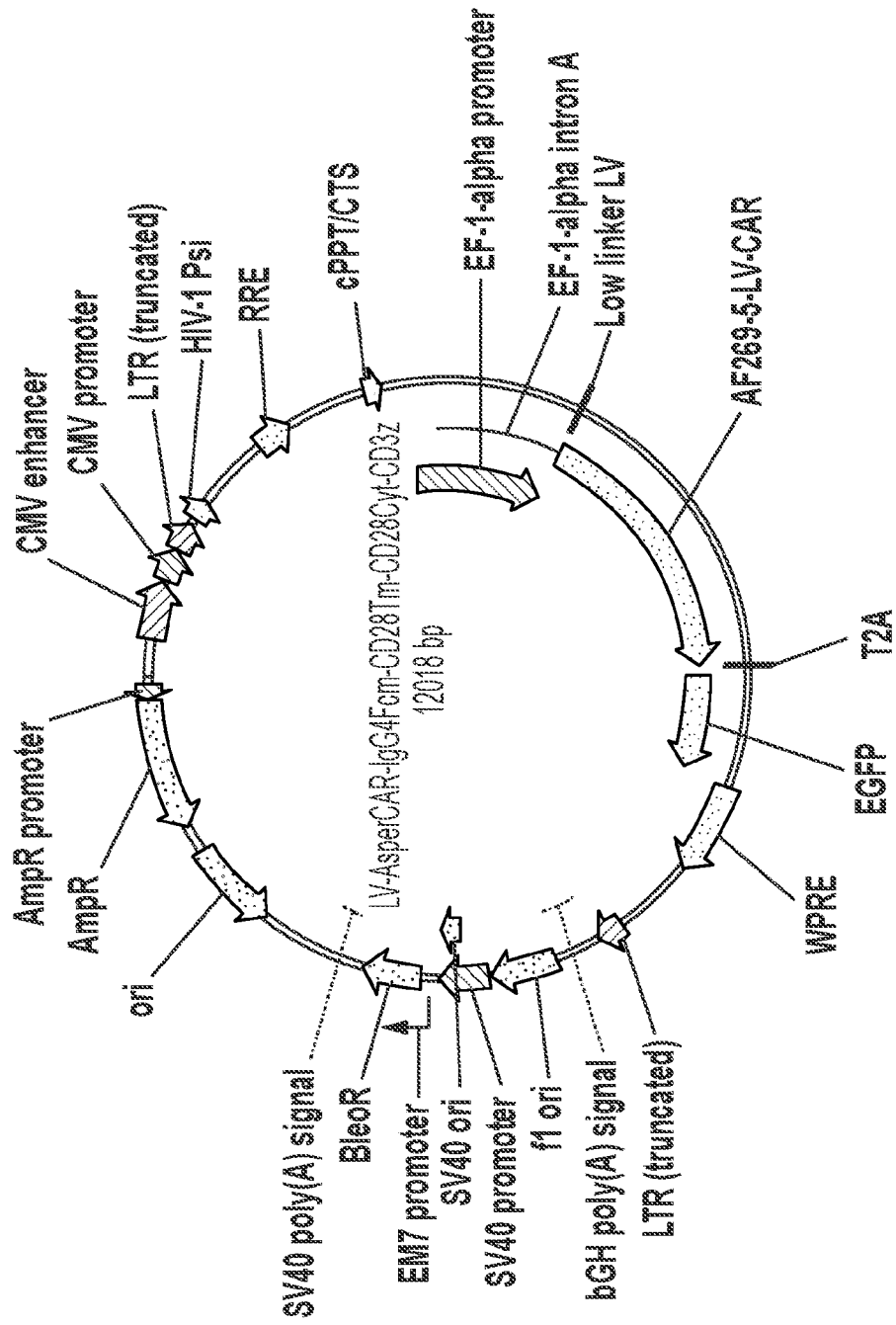
FIG. 3: Schematic for CAR expression lentiviral vector of AF-269-5 CAR (Asp-AF-269-5-scFv-IgG4M-28-3ζ CAR) and its domains.

In certain embodiments, the present disclosure provides fungal antigen specific immune cells, which may be used for the treatment of fungal infections. Specifically, the present disclosure provides CARs which target *Aspergillus* antigen p60 which can be activated upon target recognition and release cytolytic granules, such as perforin, antibacterial peptides, and granulysin, to control fungal growth. The mannan CARs provided herein can target and disrupt mature hyphae.

Accordingly, further provided herein is a monoclonal antibody against *Aspergillus fumigatus*. The AF-269-5 monoclonal antibody (mAb) can be used as diagnostic agent, such as to identify the *Aspergillus* species, or as a therapeutic agent, such as to target the *Aspergillus* sp. and modulate its growth properties. The antibody or fragment thereof may be used as as a carrier agent, such as to deliver a payload of anti-fungals to mycosis either by direct conjugation or with other bodies such as liposomes and nanoparticles. The AF-269-5 antibody, such as the scFv, may be used to make AF269-5 CAR immune cells which can be used to treat invasive fungal infections, such as infections caused by various *Aspergillus* fungal strains.

Immune cells may be engineered to express the *Aspergillus* CARs, such as AF-269-5 CARs, provided herein, such as by lentiviral vectors. The vector may be electroporated into the immune cells, such as T cells or NK cells, and used to generate CAR immune cells, such as within 2-10 days. For preventive therapy, the immune cells can be infused to patients next day. The subject may be administered the anti-fungal CAR immune cell therapy in combination with an anti-fungal agent, an anti-viral agent, an immunosuppressive agent, a calcineurin inhibitor, and/or other CAR immune cells, such as CAR T cells. The therapy may be used for the treatment of fungal infections or cancer.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. The terms "about", "substantially" and "approximately" mean, in general, the stated value plus or minus 5%.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extra-chromosomal DNA molecule separate from the chromosomal DNA that is capable of replicating independently of the chromosomal DNA. In certain cases, it is circular and double-stranded.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

An "epitope" is the site on an antigen recognized by an antibody as determined by the specificity of the amino acid sequence. Two antibodies are said to bind to the same epitope if each competitively inhibits (blocks) binding of the other to the antigen as measured in a competitive binding assay. Alternatively, two antibodies have the same epitope if most amino acid mutations in the antigen that reduce or eliminate binding of one antibody reduce or eliminate binding of the other. Two antibodies are said to have overlapping epitopes if each partially inhibits binding of the other to the antigen, and/or if some amino acid mutations that reduce or eliminate binding of one antibody reduce or eliminate binding of the other.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

"Treatment" or "treating" includes (1) inhibiting a disease in a subject or patient experiencing or displaying the pathology or symptomatology of the disease (e.g., arresting further development of the pathology and/or symptomatology), (2)

ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the term "framework region(s)" refers to regions of the variable region of an antibody which act as a scaffold for the CDRs. Thus, the framework regions may comprise the non-CDR sequences of the variable light chain and variable heavy chain. The CDRs of a variable region may be determined by methods known in the art, such as by using the Kabat numbering system as described in Sela-Culang et al., 2013; incorporated herein by reference in its entirety. The system described by Kabat (CITE) not only provides an unambiguous residue numbering system applicable to any variable region of an antibody, but also provides precise residue boundaries defining the three CDRs.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

The term "chimeric antigen receptors (CARs)," as used herein, may refer to artificial T cell receptors, chimeric T cell receptors, or chimeric immunoreceptors, for example, and encompass engineered receptors that graft an artificial specificity onto a particular immune effector cell. CARs may be employed to impart the specificity of a monoclonal antibody onto immune cells, such as macrophages, B cells, endothelial cells, activated T cells, γζ-T cells, NK cells, NKT cells and all immune cell subsets, thereby allowing a large number of specific immune cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling domains derived from co-stimulatory receptors, such as CD3ζ, FcR, CD27, CD28, CD30, CARD-9 and 10, CD137, DAP10, Toll-like receptor family, and/or OX40, and NK cell activating receptors such as NKp30, NKp46, NKp44, DAP12, NKG2D, CD160, KIR2DS1, CD16, CD226, NKp80, CS1 (CD319), and 2B4 (CD244). In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

The term "antigen presenting cells (APCs)" refers to a class of cells capable of presenting one or more antigens in the form of peptide-MHC complex recognizable by specific effector cells of the immune system, and thereby inducing an effective cellular immune response against the antigen or antigens being presented. APCs can be intact whole cells such as macrophages, B-cells, endothelial cells, activated T-cells, and dendritic cells; or other molecules, naturally occurring or synthetic, such as purified MHC Class I molecules complexed to β2-microglobulin. While many types of cells may be capable of presenting antigens on their cell surface for T-cell recognition, only dendritic cells have the capacity to present antigens in an efficient amount to activate naive T-cells for cytotoxic T-lymphocyte (CTL) responses.

The term "culturing" refers to the in vitro maintenance, differentiation, and/or propagation of cells in suitable media. By "enriched" is meant a composition comprising cells present in a greater percentage of total cells than is found in the tissues where they are present in an organism.

A polynucleotide or polynucleotide region (or a polypeptide or polypeptide region) has a certain percentage (for example, 80%, 85%, 90%, or 95%) of "sequence identity" or "homology" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+SwissProtein+SPupdate+ PIR.

II. AF269-5 ANTIBODY

Certain embodiments of the present disclosure provide an isolated monoclonal antibody, wherein the antibody specifically binds to *Aspergillus* antigen p60. In some aspects, the antibody comprises (a) a first $V_H$ CDR at least 80% identical to $V_H$ CDR1 of AF269-5 (SEQ ID NO: 7); (b) a second $V_H$ CDR at least 80% identical to $V_H$ CDR2 of AF269-5 (SEQ ID NO: 8); (c) a third $V_H$ CDR at least 80% identical to $V_H$ CDR3 of AF269-5 (SEQ ID NO: 9); (d) a first $V_L$ CDR at least 80% identical to $V_L$ CDR1 of AF269-5 (SEQ ID NO: 2); (e) a second $V_L$ CDR at least 80% identical to $V_L$ CDR2 of AF269-5 (SEQ ID NO: 3); and (f) a third $V_L$ CDR at least 80% identical to $V_L$ CDR3 of AF269-5 (SEQ ID NO: 4).

In some aspects, the antibody comprises (i) a $V_H$ domain at least about 80% identical to the $V_H$ domain of AF269-5 (SEQ ID NO: 6) and a $V_L$ domain at least about 80% identical to the $V_L$ domain of AF269-5 (SEQ ID NO: 1). In a specific aspect, the antibody comprises a $V_H$ domain identical to the $V_H$ domain of AF269-5 (SEQ ID NO: 6) and a $V_L$ domain identical to the $V_L$ domain of AF269-5 (SEQ ID NO: 1). In one specific aspect, the antibody is the AF269-5 antibody. In further aspects, the antibody is recombinant.

In additional aspects, the antibody is an IgG, IgM, IgA or an antigen binding fragment thereof. In certain aspects, the antibody is a Fab', a F(ab')2, a F(ab')3, a monovalent scFv, a bivalent scFv, or a single domain antibody. In specific aspects, the antibody may be a human, humanized antibody or de-immunized antibody. In some aspects, the antibody is conjugated to an imaging agent, a chemotherapeutic agent, a toxin or a radionuclide.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Embodiments provide antibodies and antibody-like molecules against *Aspergillus* antigenp60, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

III. IMMUNE CELLS

Certain embodiments of the present disclosure concern immune cells which express an AF269-5 CAR. The immune cells may be T cells (e.g., regulatory T cells, CD4$^+$ T cells, CD8$^+$ T cells, or gamma-delta T cells), NK cells, invariant NK cells, NKT cells, stem cells (e.g., mesenchymal stem cells (MSCs), B cells or induced pluripotent stem (iPSC) cells). In some embodiments, the cells are monocytes or granulocytes, e.g., myeloid cells, macrophages, neutrophils, dendritic cells, mast cells, eosinophils, and/or basophils. In particular aspects, the immune cells for CAR expression are T cells (e.g., αβ T cells, such as CD4 and CD8 cells, γδ T cells, regulatory T cells, T17 cells, Tfh cells, Th1, and Th2 cells), NK cells, macrophages, dendritic cells (e.g., derived from autologous PBMC, cord blood PBMC and donor PBMC), lymphocytes and myelocytes, such as derived from the tumor microenvironment. Other cells include T cell cancer cell lines, such as Jurkat cells, and NK cell lines, such as NK-92 and its derivatives and KHYG-1 and its derivatives, and macrophage cell lines, such as U937. Also provided herein are methods of producing and engineering the immune cells as well as methods of using and administering the cells for adoptive cell therapy, in which case the cells may be autologous or allogeneic. Thus, the immune cells may be used as immunotherapy, such as to treat fungal infections.

The immune cells may be isolated from subjects, particularly human subjects. The immune cells can be obtained from a subject of interest, such as a subject suspected of having a particular disease or condition, a subject suspected of having a predisposition to a particular disease or condition, or a subject who is undergoing therapy for a particular disease or condition. Immune cells can be collected from any location in which they reside in the subject including, but not limited to, blood, cord blood, spleen, thymus, lymph nodes, and bone marrow. The isolated immune cells may be used directly, or they can be stored for a period of time, such as by freezing.

The immune cells may be enriched/purified from any tissue where they reside including, but not limited to, blood (including blood collected by blood banks or cord blood banks), spleen, bone marrow, tissues removed and/or exposed during surgical procedures, and tissues obtained via biopsy procedures. Tissues/organs from which the immune cells are enriched, isolated, and/or purified may be isolated from both living and non-living subjects, wherein the non-living subjects are organ donors.

The population of immune cells can be obtained from a subject in need of therapy or suffering from a disease associated with reduced immune cell activity. Thus, the cells will be autologous to the subject in need of therapy. Alternatively, the population of immune cells can be obtained from a donor, preferably a histocompatibility matched donor. The immune cell population can be harvested from the peripheral blood, cord blood, bone marrow, spleen, or any other organ/tissue in which immune cells reside in said subject or donor.

When the population of immune cells is obtained from a donor distinct from the subject, the donor is preferably allogeneic, provided the cells obtained are subject-compatible in that they can be introduced into the subject. Allogeneic donor cells are may or may not be human-leukocyte-antigen (HLA)-compatible.

In some embodiments, the immune cells are T cells. Several basic approaches for the derivation, activation and expansion of functional anti-tumor effector cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods described herein.

In some embodiments, the T cells are derived from the blood, bone marrow, lymph, umbilical cord, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., $CD4^+$ and/or $CD8^+$ T cells) are naive T ($T_N$) cells, effector T cells ($T_{EFF}$), memory T cells and sub-types thereof, such as stem cell memory T ($TSC_M$), central memory T ($TC_M$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ T cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2).

The cultured T cells can be pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell of the cancer, which can be optionally expressed from a vector, such as an human leukocyte antigen A2 (HLA-A2) binding peptide, in the presence of a T cell growth factor.

The autologous T cells can be modified to express a T cell growth factor that promotes the growth and activation of the autologous T cells. Suitable T cell growth factors include, for example, interleukin (IL)-2, IL-7, IL-15, and IL-12. Suitable methods of modification are known in the art. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, N.Y., 1994. In particular aspects, modified autologous T cells express the T cell growth factor at high levels.

IV. CHIMERIC ANTIGEN RECEPTORS

The present disclosure provides AF269-5 CARs which comprise the *Aspergillus* p60 antigen antigen binding domain, such as an AF269-5 scFv. The anti-scFv may have 80%, 85%, 86%, 87%, 88%, 89%, 90%, 91%, 92%, 93%, 94%, 95%, 96%, 97%, 98%, or 100% sequence identity to the scFv of SEQ ID NOs: 1 and 5 (i.e., the scFv of the AF269-5 antibody). The AF269-5 CAR may have 80%, 85%, 86%, 87%, 88%, 89%, 90%, 91%, 92%, 93%, 94%, 95%, 96%, 97%, 98%, or 100% sequence identity to the nucleotide sequence of SEQ ID NO:11 or the amino acid sequence of SEQ ID NO:12. In some embodiments, the CAR contains an extracellular antigen-recognition domain that specifically binds to *Aspergillus* specific antigen p60.

In some embodiments, the chimeric antigen receptor comprises: a) an intracellular signaling domain, b) a hinge and transmembrane domain and c) an extracellular domain comprising an antigen binding region.

In some embodiments, the engineered antigen receptors include chimeric antigen receptors (CARs), including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects, via linkers and/or transmembrane domain(s). Such molecules typically mimic or approximate a signal through a natural antigen receptor, a signal through such a receptor in combination with a costimulatory receptor, and/or a signal through a costimulatory receptor alone.

Certain embodiments of the present disclosure concern the use of nucleic acids, including nucleic acids encoding an antigen-specific CAR polypeptide, including a CAR that has been humanized to reduce immunogenicity (hCAR), comprising an intracellular signaling domain, a transmembrane domain, and an extracellular domain comprising one or more signaling motifs. In certain embodiments, the CAR may recognize an epitope comprising the shared space between one or more antigens. In certain embodiments, the binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor.

It is contemplated that the human CAR nucleic acids may be human genes used to enhance cellular immunotherapy for human patients. In a specific embodiment, the invention includes a full-length CAR cDNA or coding region. The antigen binding regions or domain can comprise a fragment of the $V_H$ and $V_L$ chains of a single-chain variable fragment (scFv) derived from a particular human monoclonal antibody. The fragment can also be any number of different antigen binding domains of a human antigen-specific antibody. In a more specific embodiment, the fragment is an antigen-specific scFv encoded by a sequence that is optimized for human codon usage for expression in human cells.

The arrangement could be multimeric, such as a diabody or multimers. The multimers are most likely formed by cross pairing of the variable portion of the light and heavy chains into a diabody. The hinge portion of the construct can have multiple alternatives from being totally deleted, to having the first cysteine maintained, to a proline rather than a serine substitution, to being truncated up to the first cysteine. The Fc portion can be deleted. Any protein that is stable and/or dimerizes can serve this purpose. One could use just one of the Fc domains, e.g., either the CH2 or CH3 domain from human immunoglobulin. One could also use the hinge, CH2 and CH3 region of a human immunoglobulin that has been modified to improve dimerization. One could also use just the hinge portion of an immunoglobulin. One could also use portions of CD8alpha.

In some embodiments, the CAR nucleic acid comprises a sequence encoding other costimulatory receptors, such as a transmembrane domain and a modified CD28 intracellular signaling domain. Other costimulatory receptors include, but are not limited to one or more of CD28, CD27, OX-40 (CD134), DAP10, DAP12, and 4-1BB (CD137). In addition to a primary signal initiated by CD3ζ, an additional signal provided by a human costimulatory receptor inserted in a human CAR is important for full activation of NK cells and could help improve in vivo persistence and the therapeutic success of the adoptive immunotherapy.

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into immune cells as naked DNA or in a suitable vector. Methods of stably transfecting cells by electroporation using naked DNA are known in the art. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into immune cells. Suitable vectors for use in accordance with the method of the present disclosure are non-replicating in the immune cells. A large number of vectors are known that are based on viruses, where the copy number of the virus maintained in the cell is low enough to maintain the viability of the cell, such as, for example, vectors based on HIV, SV40, EBV, HSV, or BPV.

In some aspects, the antigen-specific binding, or recognition component is linked to one or more transmembrane and intracellular signaling domains. In some embodiments, the CAR includes a transmembrane domain fused to the extracellular domain of the CAR. In one embodiment, the transmembrane domain that naturally is associated with one of the domains in the CAR is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD16, CD22, CD33, CD37, CD64, CD80, CD86, CD134, CD137, CD154, ICOS/CD278, GITR/CD357, NKG2D, and DAP molecules. Alternatively, the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain.

V. METHODS OF USE

Fungal infections pose a significant threat to the human population by affecting over a billion people worldwide. Despite the availability of anti-fungal drugs, invasive fungal infections are associated with high mortality rates worldwide, causing an estimated 1.5 million deaths each year, a number comparable to tuberculosis. Thus, the present disclosure further provides methods of treating fungal infections by administering an effective amount of AF296-5 CAR-cell, such as CAR-T cells or CAR-NK cells, to a subject. The subject may be an immunocompromised patients, such as those living with HIV/AIDs, cancer patients who are receiving chemotherapy, or solid organ transplant patients who are taking immunosuppressive drugs.

In certain embodiments of the present disclosure, immune cells are delivered to an individual in need thereof, such as an individual that has cancer or a fungal infection. The cells then enhance the individual's immune system to attack the respective cancer or pathogenic cells. In some cases, the individual is provided with one or more doses of the immune cells. In cases where the individual is provided with two or more doses of the immune cells, the duration between the administrations should be sufficient to allow time for propagation in the individual, and in specific embodiments the duration between doses is 1, 2, 3, 4, 5, 6, 7, or more days.

In yet another embodiment, the subject is the recipient of a transplanted organ or stem cells and immune cells are used to prevent and/or treat rejection. In particular embodiments, the subject has or is at risk of developing graft versus host disease. Any of the populations of immune cells disclosed herein can be utilized. Examples of a transplanted organ include a solid organ transplant, such as kidney, liver, skin, pancreas, lung and/or heart, or a cellular transplant such as islets, hepatocytes, myoblasts, bone marrow, or hematopoietic or other stem cells. The transplant can be a composite transplant, such as tissues of the face. Immune cells can be administered prior to transplantation, concurrently with transplantation, or following transplantation. In some embodiments, the immune cells are administered prior to the transplant, such as at least 1 hour, at least 12 hours, at least 1 day, at least 2 days, at least 3 days, at least 4 days, at least 5 days, at least 6 days, at least 1 week, at least 2 weeks, at least 3 weeks, at least 4 weeks, or at least 1 month prior to the transplant. In one specific, non-limiting example, administration of the therapeutically effective amount of immune cells occurs 3-5 days prior to transplantation.

In certain embodiments, a growth factor that promotes the growth and activation of the immune cells is administered to the subject either concomitantly with the immune cells or subsequently to the immune cells. The immune cell growth factor can be any suitable growth factor that promotes the growth and activation of the immune cells. Examples of suitable immune cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2.

Therapeutically effective amounts of immune cells can be administered by a number of routes, including parenteral administration, for example, intravenous, intraperitoneal, intramuscular, intrasternal, or intraarticular injection, or infusion.

The therapeutically effective amount of immune cells for use in adoptive cell therapy is that amount that achieves a desired effect in a subject being treated. For instance, this can be the amount of immune cells necessary to inhibit advancement, or to cause regression of a fungal infection, or which is capable of relieving symptoms caused by a fungal infection, such as pain and inflammation. It can be the amount necessary to relieve symptoms associated with inflammation, such as pain, edema and elevated temperature. It can also be the amount necessary to diminish or prevent rejection of a transplanted organ.

The immune cell population can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of immune cells will be dependent on the subject being treated, the severity and type of the affliction, and the manner of administration. In some embodiments, doses that could be used in the treatment of human subjects range from at least $3.8 \times 10^4$, at least $3.8 \times 10^5$, at least $3.8 \times 10^6$, at least $3.8 \times 10^7$, at least $3.8\times10^8$, at least $3.8\times10^9$, or at least $3.8\times10^{10}$ immune cells/m². In a certain embodiment, the dose used in the treatment of human subjects ranges from about $3.8\times10^9$ to about $3.8\times10^{10}$ immune cells/m². In additional embodiments, a therapeutically effective amount of immune cells can vary from about $5\times10^6$ cells per kg body weight to about $7.5\times10^8$ cells per kg body weight, such as about $2\times10^7$ cells to about $5\times10^8$ cells per kg body weight, or about $5\times10^7$ cells to about $2\times10^8$ cells per kg body weight. The exact amount of immune cells is readily determined by one of skill in the art based on the age, weight, sex, and physiological condition of the subject. Effective doses can be extrapolated from dose-response curves derived from in vitro or animal model test systems.

The immune cells may be administered in combination with one or more other therapeutic agents for the treatment of the fungal infection. Combination therapies can include, but are not limited to, one or more anti-microbial agents (for example, antibiotics, anti-viral agents and anti-fungal agents, such as Amphotericin B, Caspofungin, Isavuconazole, or Posaconazole, anti-tumor agents (for example, fluorouracil, methotrexate, paclitaxel, fludarabine, etoposide, doxorubicin, or vincristine), fungal cell wall degrading enzymes such as Chitinase and β-glucanase; non-steroidal anti-inflammatory agents such as acetylsalicylic acid, ibuprofen or naproxen sodium), cytokines (for example, interleukin-10 or transforming growth factor-beta), hormones (for example, estrogen), or a vaccine. Other therapies may comprise antibodies (e.g., recognizing CD3, CD4, CD40, CD154, CD45, IVIG, or B cells); or chemokines, interleukins or their inhibitors (e.g., BAFF or IL-2) can be administered. Such additional pharmaceutical agents can be administered before, during, or after administration of the immune cells, depending on the desired effect. This administration of the cells and the agent can be by the same route or by different routes, and either at the same site or at a different site.

Also provided herein are pharmaceutical compositions and formulations comprising immune cells (e.g., T cells or NK cells) and a pharmaceutically acceptable carrier.

Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences $22^{nd}$ edition, 2012), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Development of AF269-5 CAR

Figure 4A:
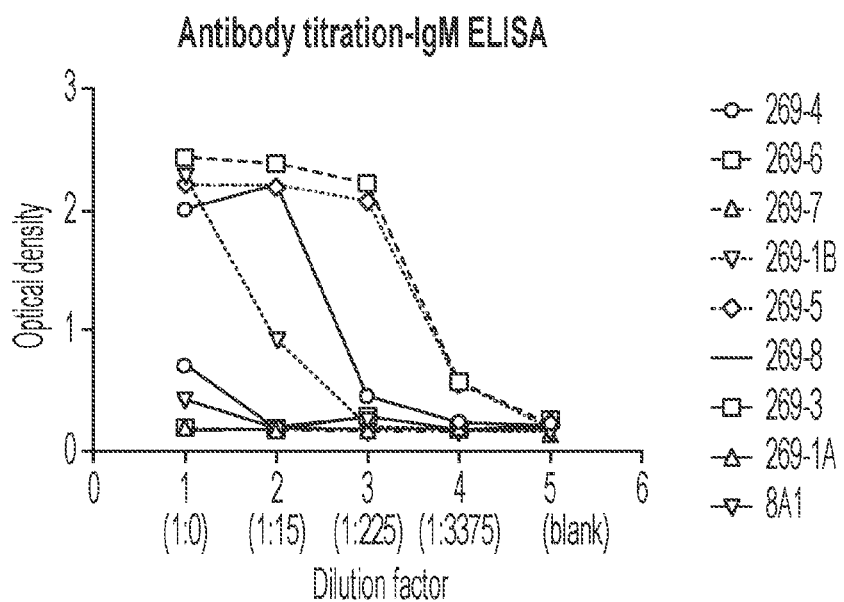
FIGS. 4A-4B: Hybridoma supernatant titration by ELISA using (A) anti-IgM as a secondary antibody or (B) IgG as a secondary antibody.
Figure 4B:
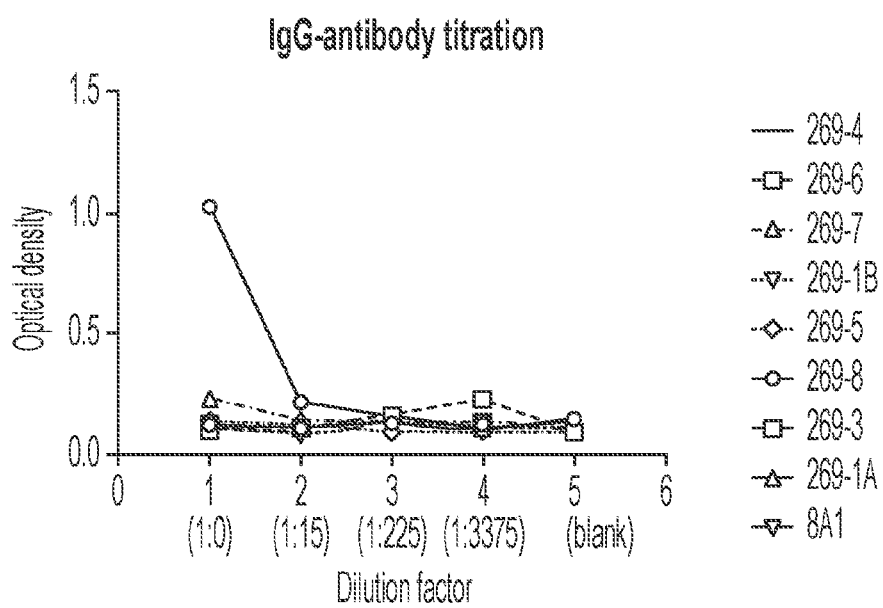
Figure 5:
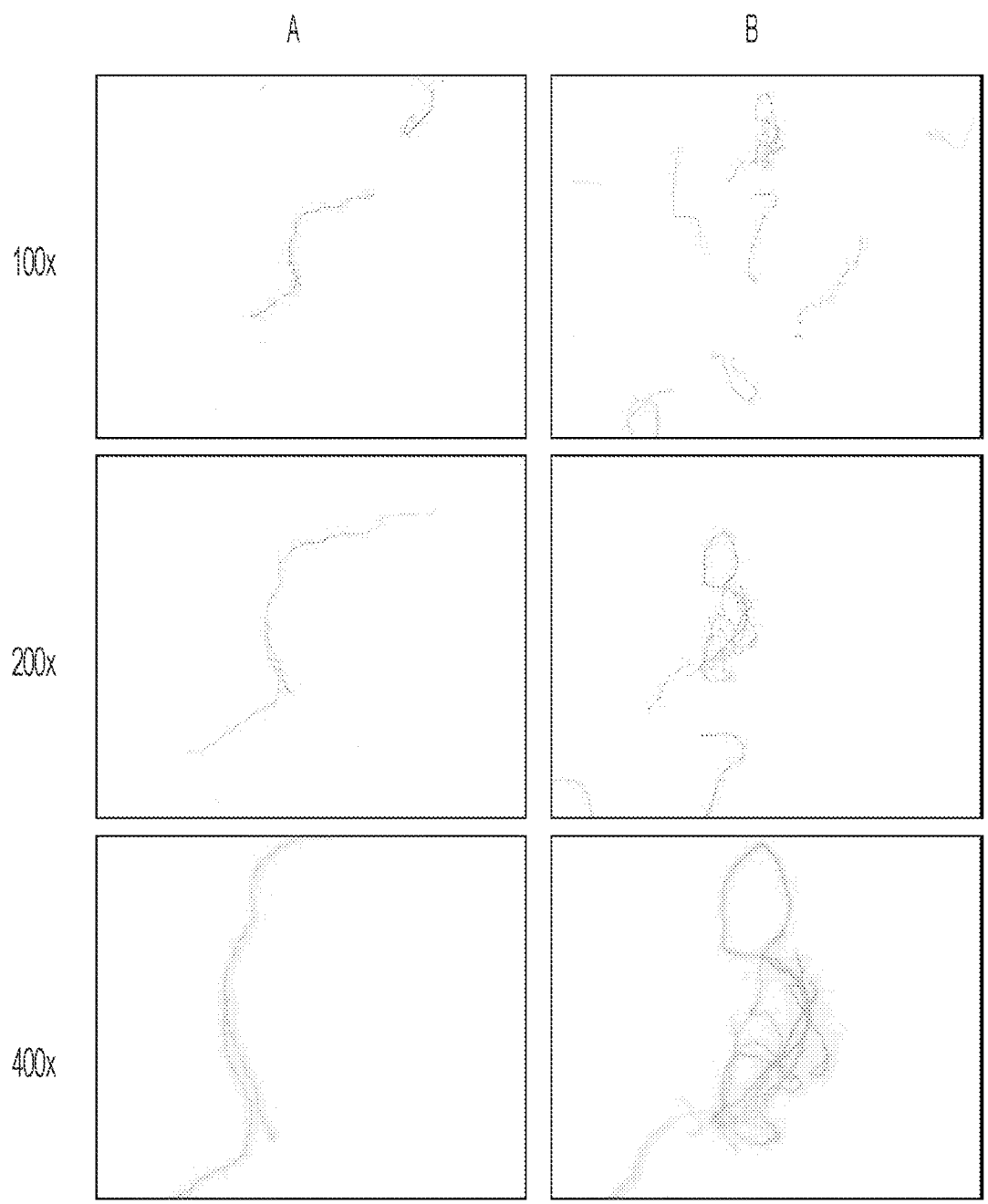
FIG. 5: Fluorescence microscopy analysis of AF293 strain mycelium. Few condia were seeded per well in an 8 well chambered glass slide and incubated overnight. AF269-5 antibody was incubated at 1:100 dilution for 1h. Samples were washed 3 times before the addition of FITC-conjugated goat anti-mouse-IgM secondary antibody at 1:1000 dilution, washed 3 times, and imaged using fluorescence microscopy. AF269-5 stains both young and mature *Aspergillus fumigatus*.
Figure 6:
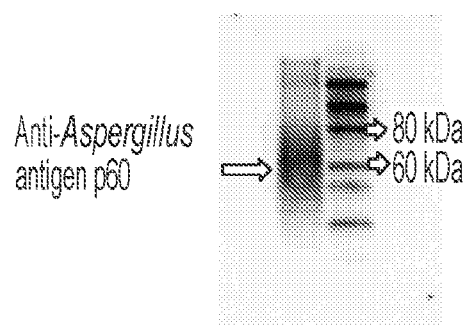
FIG. 6: Western blot analysis. 1 μg of *Aspergillus* lysate was loaded on a 10% SDS gel, electrophoresed, and transferred to a nitrocellulose membrane. After blocking with 0.5% BSA for 1 hour at RT, the membrane was incubated with AF269-5 antibody at 1-500 dilution for 1 hour. After 3 washes with PBS, the blot was incubated with anti-mouse IgM-HRP conjugated secondary antibody, washed 3 times, and developed by the chemiluminescent method using manufacturer protocol. AF269-5 antibody recognized a 60 kDa protein, noted as *Aspergillus* (Asp) antigen p60.

AF269-5 monoclonal antibody was produced and is provided herein as AF269-5. Hybridoma titration was performed by ELISA using anti-IgM and anti-IgG secondary antibodies as shown in FIGS. 4A-4B. The AF-269-5 monoclonal antibody can be used to identify *Aspergillus* sp.

The scFv of the AF269-5 antibody was used to develop the AF269-5 CARs by fusing the scFv region of the AF269-5 antibody with other signaling domains as described in general CARs structure (Table 1). The AF269-5 CARs comprise CARs targeting the *Aspergillus* antigen p60 present on the fungal cell wall.

TABLE 1

Design elements used to generate glycan CARs using gateway system

| Extra cellular Domain | Hinge | TM-domain | Signaling domain |
|---|---|---|---|
| 18B7-scFv | 12 aa | 28 | CD28 & CD3-ζ |
| | 119 aa | CD8a | CD134 & CD3-ζ |
| | 232 aa | CD134 | CD137 & CD3-ζ |
| | | CD137 | CD28 & CD134 & CD3-ζ |
| | | TLR | CD28 & CD137 & CD3-ζ |
| | | | CD134 & CD137 & CD3-ζ |
| | | | CD28 & CD134 & CD137 & CD3-ζ |
| | | | TRAM, MyD88, TRAF6 |

Generation of AF269-5 Antibody

Mice: BALB/c mice for antibody development were purchased from Charles River. Mice were housed in a pathogen-free animal facility according to institutional guidelines. All animal studies were conducted under an approved protocol by the Institutional Animal Care and Use Committee (IACUC).

Generation of Antibody-producing hybridomas: Immunization and hybridoma generation procedures were conducted at the University of Texas M.D. Anderson Cancer Center-CCSG Monoclonal Antibody Core Facility—following established protocols (Jiemiao et al., 2014); Voo et al., 2013; Qin et al., 2018). Briefly, two 6-week-old female BALB/c mice were immunized once every 3 days with the *Aspergillus Fumigatus* cell lysate by five injections of 20 ul each of the solution emulsified with adjuvant on the footpad. After the fifth injection, serum samples were obtained from both mice to confirm by ELISA, the presence of serum antibodies against the target. Extra boosts were administered as required. Popliteal lymph nodes from the immunized mice were harvested around day 20 and lymph cells were fused with Sp2/0 myeloma to establish hybridomas, plated under selection media (HAT). Screening for selection of positive clones against the phospho-peptide, was performed by ELISA using non-phosphorylated peptide as negative control. Initial selected clones were then subcloned and re-screened by ELISA to select those with the highest affinity. After selection of hybridoma candidates master cells, antibodies were purified using Mab Select SuRe antibody purification resin (GE healthcare) and eluted with low pH Ag/Ab elution buffer. Validation and quality control tests of purified antibody: specificity (binding screening by ELISA), purity (SDS-PAGE), endotoxin (Lonza Endotoxin kit) and isotype (ELISA Sigma) were conducted following recommendations of Rigor and reproducibility by International Working Group for Antibody Validation (*Nature Methods*, 2016).

ELISA Screening: Costar EIA/RIA plates (Fisher Scientific, Hampton, NH) were coated with 0.1 ug/ml of phospho-peptide or negative control and allowed to dry overnight. Wells were blocked by incubation in PBST containing 2% bovine serum albumin for 1 hour at room temperature. Culture supernatant from hybridoma plates (100 μl) was then added, incubated for 1 hour at room temperature and then washed with PBST 3 times. Goat anti-mouse immunoglobulin G (IgG) Fc, horseradish peroxidase (HRP) conjugate (100 μl; Jackson Immunoresearch: 115-035-071) was then added, and incubated at room temperature for 1 hour and washed 5 times with PBST before the substrate was added. Absorbance was read at 450.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

International Working Group for Antibody Validation, *Nature Methods* 13: 823-827, 2016.
Jiemiao et al., Biol Proced Online. 16(1):3, 2014.
Qin et al., Clin Cancer Res. 24(5):1114-1123, 2018.
Voo et al., J Immunol. 191(7):3641-50, 2013.

What is claimed is:

1. An isolated monoclonal antibody, wherein the antibody specifically binds to *Aspergillus* antigen p60 and comprises:
   (a) a first $V_H$ CDR encoded by SEQ ID NO: 7;
   (b) a second $V_H$ CDR encoded by SEQ ID NO: 8;
   (c) a third $V_H$ CDR encoded by SEQ ID NO: 9;
   (d) a first $V_L$ CDR encoded by SEQ ID NO: 2;
   (e) a second $V_L$ CDR encoded by SEQ ID NO: 3; and
   (f) a third $V_L$ CDR encoded by SEQ ID NO: 4.

2. The antibody of claim 1, wherein the antibody comprises a $V_H$ domain at least about 80% identical to the $V_H$ domain encoded by SEQ ID NO: 6 and a $V_L$ domain at least about 80% identical to the $V_L$ domain encoded by SEQ ID NO: 1.

3. The antibody of claim 1, wherein the antibody comprises a $V_H$ domain identical to the $V_H$ domain encoded by SEQ ID NO: 6 and a $V_L$ domain identical to the $V_L$ domain encoded by SEQ ID NO: 1.

4. The antibody of claim 1, wherein the amino acid sequences of the antibody comprise a $V_H$ domain at least about 80% identical to the $V_H$ domain of AF269-5 (SEQ ID NO: 10) and a $V_L$ domain at least about 80% identical to the $V_L$ domain of AF269-5 (SEQ ID NO: 5).

5. The antibody of claim 1, wherein the amino acid sequences of the antibody comprise a $V_H$ domain identical to the $V_H$ domain of AF269-5 (SEQ ID NO: 10) and a $V_L$ domain identical to the $V_L$ domain of AF269-5 (SEQ ID NO: 5).

6. The antibody of claim 1, wherein the antibody is recombinant.

7. The antibody of claim 1, wherein the antibody is a Fab', a F(ab')2, a F(ab')3, a monovalent scFv, a bivalent scFv, or a single domain antibody.

8. A composition comprising an antibody of claim 1 in a pharmaceutically acceptable carrier.

9. A recombinant polypeptide comprising an antibody $V_H$ domain comprising CDRs 1-3 of the $V_H$ domain of AF269-5 (SEQ ID NOs: 7, 8, and 9) and an antibody $V_L$ domain comprising CDRs 1-3 of the $V_L$ domain of AF269-5 (SEQ ID NOs: 2, 3, and 4).

10. The recombinant polypeptide of claim 9, comprising an antibody $V_H$ domain of AF269-5 (SEQ ID NO: 6) and an antibody $V_L$ domain of AF269-5 (SEQ ID NO: 1).

11. A method for detecting *Aspergillus* sp. comprising:
   (a) obtaining a sample from a subject;
   (b) contacting the sample with the antibody of claim 1; and
   (c) detecting binding between the antibody and *Aspergillus* sp.

12. The method of claim 11, wherein the *Aspergillus* sp. is *A. fumigatus* or *A. avis*.

13. A chimeric antigen receptor (CAR) comprising an *Aspergillus* antigen p60-binding domain comprising:
   (a) a first $V_H$ CDR encoded by SEQ ID NO: 7;
   (b) a second $V_H$ CDR encoded by SEQ ID NO: 8;
   (c) a third $V_H$ CDR encoded by SEQ ID NO: 9;
   (d) a first $V_L$ CDR encoded by SEQ ID NO: 2;
   (e) a second $V_L$ CDR encoded by SEQ ID NO: 3; and
   (f) a third $V_L$ CDR encoded by SEQ ID NO: 4.

14. The CAR of claim 13, wherein the *Aspergillus* antigen p60-binding domain is selected from the group consisting of F(ab')2, Fab', Fab, Fv, and scFv.

15. The CAR of claim 13, wherein the *Aspergillus* antigen p60-binding domain is an scFv that comprises an amino acid sequence with at least 80% sequence identity to SEQ ID NO: 12 or an scFv that is encoded by a nucleotide sequence with at least 80% sequence identity to SEQ ID NO: 11.

16. The CAR of claim 13, wherein the CAR comprises a CD28, CD8a, CD134, CD137, or TLR transmembrane domain.

17. The CAR of claim 13, wherein the CAR comprises a spacer encoded by SEQ ID NO: 15.

18. The CAR of claim 17, wherein the CAR comprises an *Aspergillus* antigen p60-binding domain scFv, a spacer, a CD28 transmembrane domain, a CD28 signaling domain, and a CD3ζ signaling domain.

19. The CAR of claim 18, wherein the CAR comprises a nucleotide sequence with at least 95% sequence identity to SEQ ID NO: 11.

20. An isolated host cell engineered to express a CAR comprising an *Aspergillus* antigen p60 binding domain according to claim 13.

* * * * *